US008585628B2

(12) United States Patent
Harris et al.

(10) Patent No.: US 8,585,628 B2
(45) Date of Patent: Nov. 19, 2013

(54) METHODS AND DEVICES FOR REGULATING THE ACTIVATION OF GHRELIN HORMONES WITHIN A STOMACH

(75) Inventors: Jason L. Harris, Mason, OH (US); Mark S. Ortiz, Milford, OH (US); Mark D. Overmyer, Cincinnati, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 62 days.

(21) Appl. No.: 13/105,006

(22) Filed: May 11, 2011

(65) Prior Publication Data
US 2011/0295286 A1 Dec. 1, 2011

Related U.S. Application Data

(60) Provisional application No. 61/348,274, filed on May 26, 2010.

(51) Int. Cl.
*A61B 19/00* (2006.01)
(52) U.S. Cl.
USPC ............................................. 604/8; 514/945
(58) Field of Classification Search
USPC ............................................. 604/8; 514/945
See application file for complete search history.

(56) References Cited

U.S. PATENT DOCUMENTS

| 7,025,791 | B2 | 4/2006 | Levine et al. | |
|---|---|---|---|---|
| 7,122,058 | B2 | 10/2006 | Levine et al. | |
| 7,267,694 | B2 | 9/2007 | Levine et al. | |
| 7,288,101 | B2 * | 10/2007 | Deem et al. | 606/153 |
| 7,329,285 | B2 | 2/2008 | Levine et al. | |
| 7,347,875 | B2 | 3/2008 | Levine et al. | |
| 7,476,256 | B2 | 1/2009 | Meade et al. | |
| 7,914,543 | B2 | 3/2011 | Roth et al. | |
| 2004/0117031 | A1 | 6/2004 | Stack et al. | |
| 2007/0060932 | A1 * | 3/2007 | Stack et al. | 606/153 |
| 2008/0086072 | A1 * | 4/2008 | Bonutti et al. | 604/21 |
| 2009/0234417 | A1 * | 9/2009 | Pastena et al. | 607/40 |

FOREIGN PATENT DOCUMENTS

WO WO 2007/121028 10/2007

OTHER PUBLICATIONS

Johnston, D. et al, "The Magenstrasse and Mill Operation for Morbid Obesity," Obesity Surgery, vol. 13 (2003) pp. 10-16.
U.S. Appl. No. 12/242,353, filed Sep. 30, 2008, Hess et al.
U.S. Appl. No. 12/242,381, filed Sep. 30, 2008, Murray.
International Search Report dated Jul. 20, 2012 for Application No. PCT/US2011/037671.

* cited by examiner

*Primary Examiner* — Leslie Deak
*Assistant Examiner* — Sara Sass
(74) *Attorney, Agent, or Firm* — Frost Brown Todd LLC

(57) ABSTRACT

Methods and devices regulate the activation of ghrelin hormones within a stomach in order to treat weight disorders, to promote learning and memory functions, to treat stress-induced depression, and to control sleep duration. In one embodiment, a method for regulating activation of ghrelin hormones within a stomach comprises a means for isolating non-activated ghrelin hormones from food content and dietary lipids within the stomach. These means for isolating may take any number of forms and may comprise one or more of a surgical procedure, an implanted device, or an ingestible substance.

18 Claims, 19 Drawing Sheets

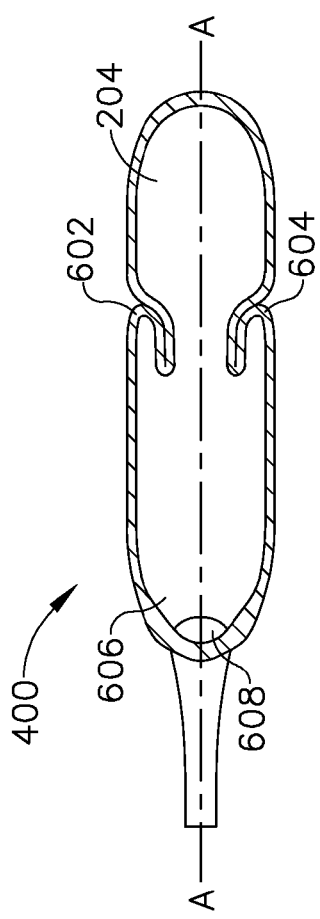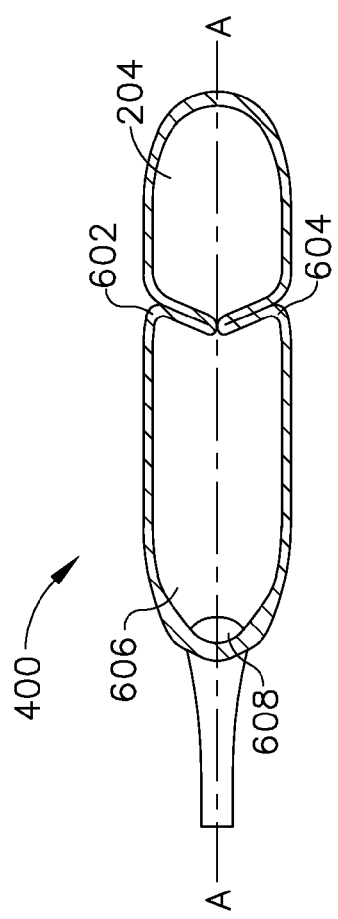

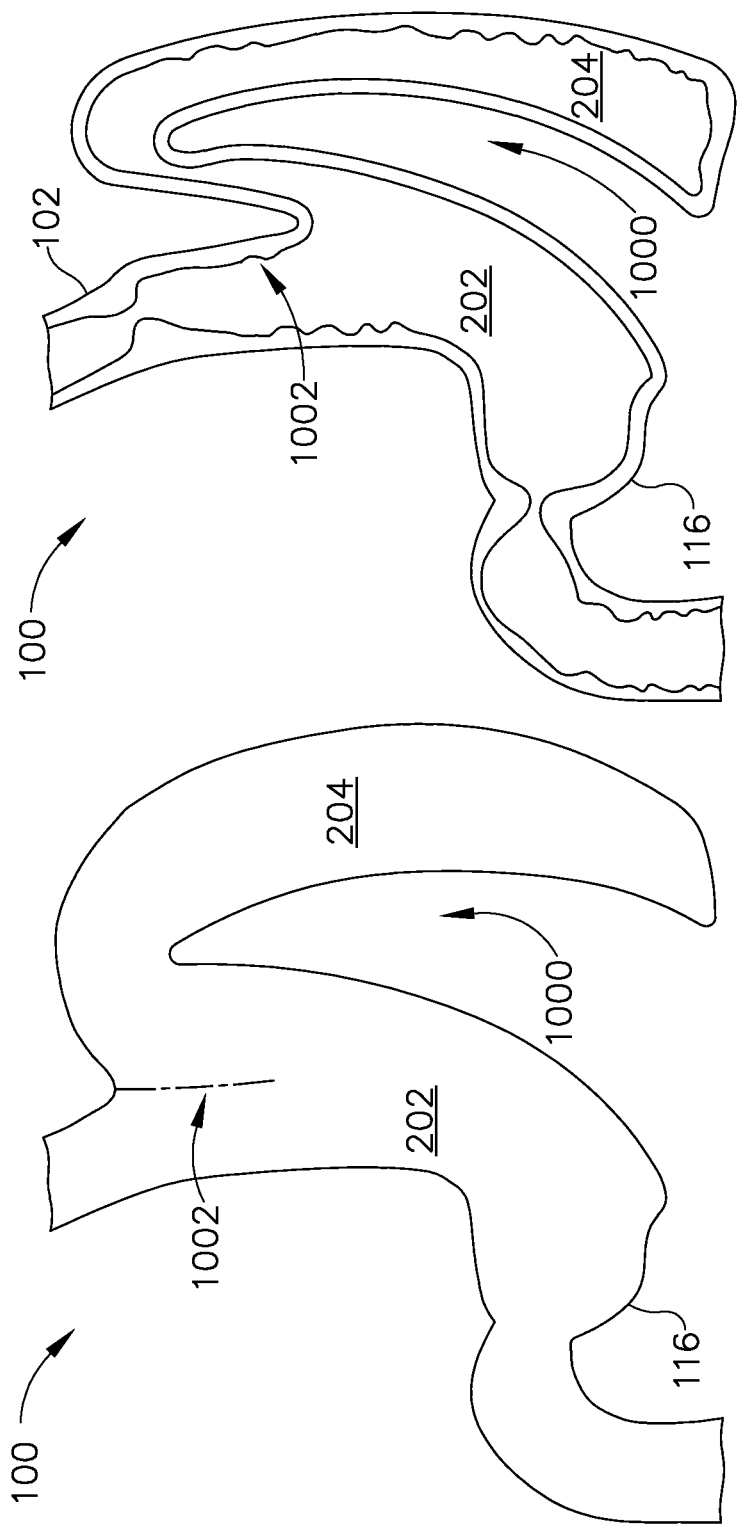

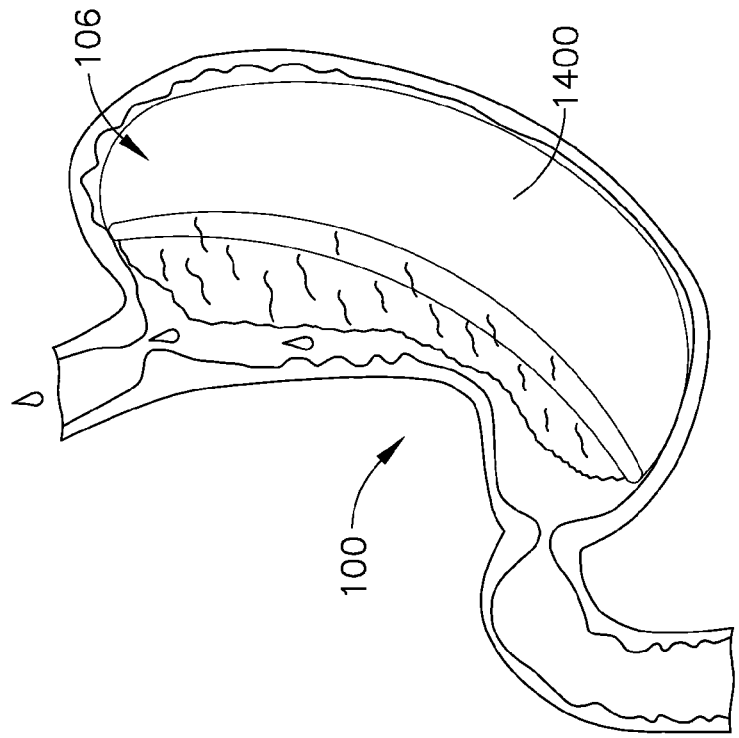
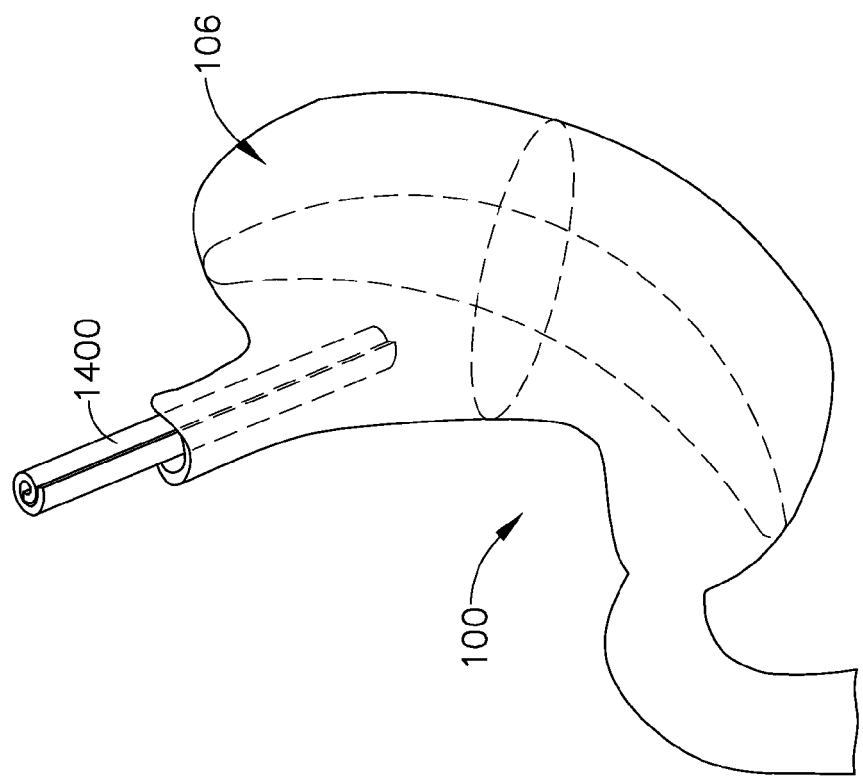
FIG. 15A
FIG. 15B

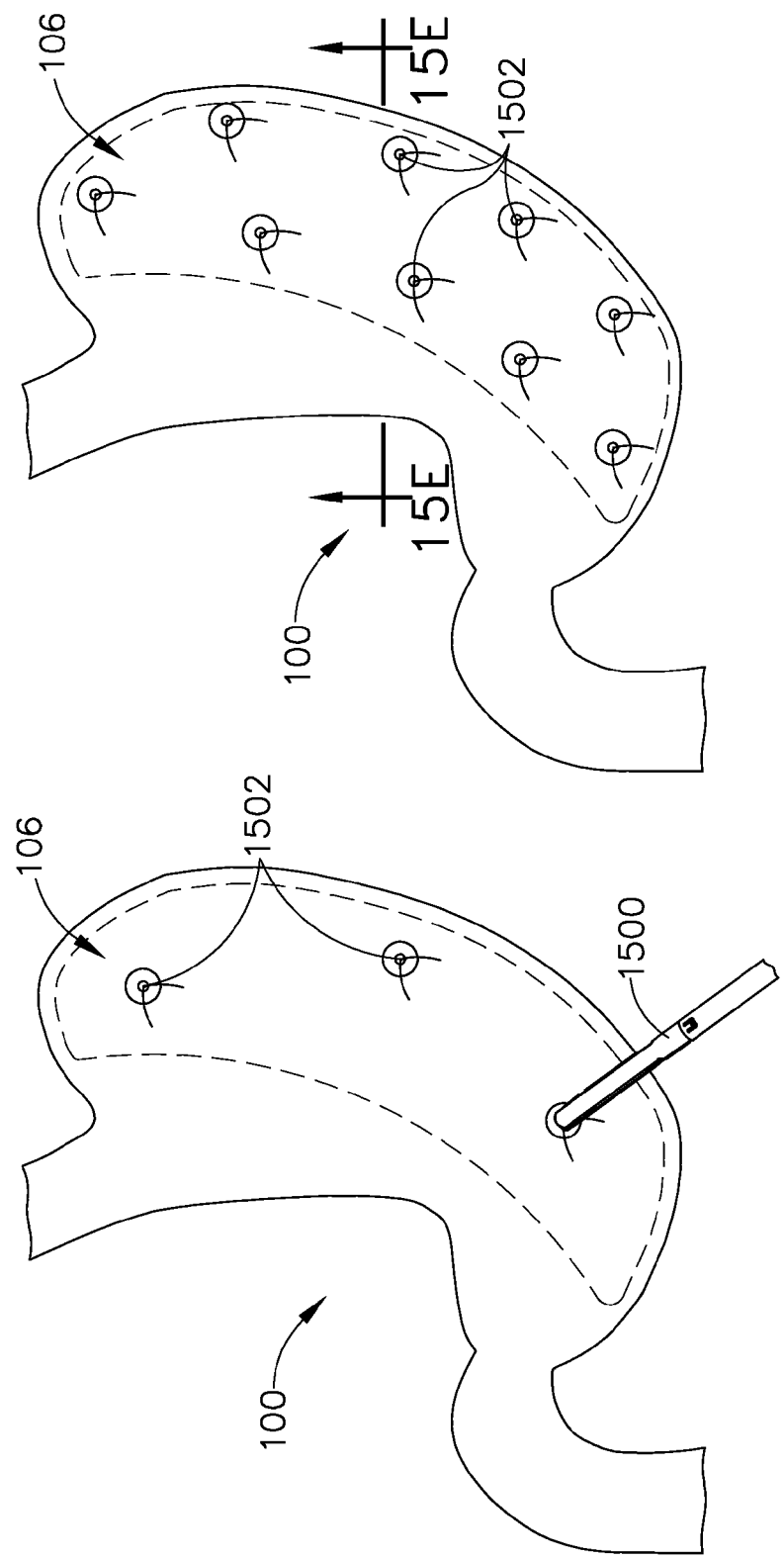

METHODS AND DEVICES FOR REGULATING THE ACTIVATION OF GHRELIN HORMONES WITHIN A STOMACH

PRIORITY

This application claims priority to U.S. Provisional Patent Application Ser. No. 61/348,274, entitled "Methods and Devices for Regulating the Activation of Ghrelin Hormones with a Stomach," filed May 26, 2010, the disclosure of which is incorporated by reference herein.

FIELD OF INVENTION

The present invention relates to methods and devices for regulating the activation of ghrelin hormones within a stomach.

BACKGROUND OF THE INVENTION

Ghrelin is a hormone produced mainly by P/D1 cells lining the majority of the human stomach. These cells are distributed throughout the stomach and portions of the duodenum, but are highly concentrated in the area of the fundus and along the greater curvature of the stomach. Ghrelin, commonly called the hunger hormone, is associated with eating and fasting cycles in the body. It has been found that ghrelin levels increase before meals and decrease after meals. Further, it has been discovered that ghrelin levels in the plasma of obese individuals are typically lower than those in leaner individuals, while those suffering from the eating disorder anorexia nervosa typically have high plasma levels of ghrelin compared to both the constitutionally thin and normal-weight controls. These findings suggest that ghrelin plays a role in weight disorders.

Additionally, increased Ghrelin levels have been linked to enhanced learning and memory, a reduction in stress-induced depression, and shorter sleep durations.

Accordingly, there remains a need for methods and devices for regulating the activation of ghrelin hormones within a stomach in order to treat weight disorders, to promote learning and memory functions, to treat stress-induced depression, and to promote healthy sleep duration.

SUMMARY OF THE INVENTION

The present invention generally provides methods and devices for regulating the activation of ghrelin hormones within a stomach in order to treat weight disorders, to promote learning and memory functions, to treat stress-induced depression, and to control sleep duration. Through recent research, it has been discovered that the enzyme Ghrelin-Octanoyl Acyl-Transferase (GOAT) mediates the control of ghrelin activation within the stomach. While dietary lipids serve as a substrate for GOAT which is used for acylation of circulating ghrelin, ghrelin acylation by GOAT may depend on the presence of specific dietary lipids. GOAT/ghrelin is a gastrointestinal lipid sensing system, yet the secretion and activation of ghrelin are two independently regulated processes. It is believed that the primary means for activating ghrelin is through the contact of the ghrelin producing cells of the stomach and/or intestines with stomach contents carrying the GOAT enzyme and dietary lipids necessary for activating ghrelin. The activated ghrelin, Human-Acyl-Ghrelin, moves from the stomach and/or intestines into the blood stream and its levels may be measured in the blood through known testing procedures. It has been found through testing that the Human Acyl-Ghrelin levels present in the blood stream decrease under fasting conditions. Accordingly, increased Human Acyl-Ghrelin levels in the blood stream may not reflect an empty stomach as previously thought; rather these increased Human Acyl-Ghrelin levels in the blood stream may actually be a signal indicating the availability of specific dietary lipids which may prepare the body for optimal nutrient partitioning and storage.

By blocking GOAT's access to ghrelin, ghrelin may be maintained in a non-activated state within the stomach, and may thereby reduce or eliminate hunger, promote learning and memory functions, treat stress-induced depression, and promote healthy sleep duration. Inversely, by facilitating GOAT's access to ghrelin, ghrelin may be maintained in an activated state within the stomach, and may thereby increase hunger or appetite, and alter healthy sleep duration. As may be appreciated, proper regulation of the activation of ghrelin hormones within a stomach may be utilized to treat or cure metabolic disorders, obesity, anorexia, depression, insomnia, learning or attention disorders, memory loss and the like.

In one embodiment, a method for regulating activation of ghrelin hormones within a stomach comprises a means for isolating ghrelin producing cells from food content and dietary lipids within the stomach is provided. These means for isolating may take any number of forms and may comprise one or more of a surgical procedure, an implanted device, or an ingestible substance.

In an exemplary method, the stomach may be partitioned into a first and second chamber; the first chamber containing and permitting flow therethrough of food content and dietary lipids; and the second chamber containing the bulk of the ghrelin hormone producing cells. Partitioning may be accomplished via a surgical procedure such as a Magenstrasse and Mill (M&M) procedure or the like, through the implanting of a device such as a gastric sleeve or the like, or through a combination of a surgical procedure and an implanted device. The Magenstrasse and Mill (M&M) procedure is an evolving gastroplasty technique wherein the greater curvature of the stomach is separated (e.g., stapled and cut) from the path of food, leaving a tube of stomach, the Magenstrasse, which is comprised of the lesser curvature. This procedure is similar to Vertical Banded Gastroplasty (VBG) except that the longitudinal separation line of the stomach extends further along the lesser curvature and into the antrum. The theory behind leaving the antral "mill" is that it will continue to serve its normal function of mixing, grinding, retropulsion, and well-orchestrated expulsion of chyme into the duodenum. Non-limiting disclosures of the M&M procedure can be found in U.S. patent application Ser. No. 12/242,381, filed Sep. 30, 2008, entitled "Methods and Devices for Performing Gastroplasties Using Multiple Port Access", now published as U.S. Pub. 2010-0081883(abandoned) and U.S. patent application Ser. No. 12/242,353, filed Sep. 30, 2008, entitled "Methods and Devices for Performing Gastrectomies and Gastroplasties" now published as U.S. Pub. 2010-0081864 (pending) which are incorporated herein by reference. A non-limiting study on the operation is incorporated herein by reference in its entirety (Johnston et. al. The Magenstrasse and Mill Operation for Morbid Obesity; Obesity Surgery 13, 10-16). Non-limiting disclosure of the implanting of a bariatric sleeve devices can be found in U.S. Pat. No. 7,476,256 B2 to Meade et al., U.S. Pat. No. 7,347,875 B2 to Levine et al., U.S. Pat. No. 7,329,285 B2 to Levine et al., U.S. Pat. No. 7,267,694 to Levine et al., U.S. Pat. No. 7,122,058 B2 to Levine et al. and U.S. Pat. No. 7,025,791 B2 to Levine et al., which are hereby incorporated by reference in their entirety. The method further includes providing a means for preventing dietary lipids from contacting ghrelin producing cells, thus preventing GOAT from utilizing the dietary lipids to activate the ghrelin. The means for preventing dietary lipids from contacting ghrelin producing cells may be accomplished by at least one of a surgical procedure and an implanted device. The surgical procedure for preventing dietary lipids from contacting ghrelin producing cells may comprise creating a passive biological one-way valve via tissue folding and/or removal. The implanted device for permitting controlled evacuation of non-activated ghrelin hormones contained within the second stomach chamber may comprise an elongate tubular device having an internal bore; the device may further include a valve assembly. Exemplary valve assemblies may comprise at least one of a duck bill valve, a ball valve, a one-way osmotic membrane, and the like.

Other means for isolating ghrelin producing cells from food content and dietary lipids within the stomach, such as introducing a substance within the stomach which substantially regulates the activation of ghrelin producing cells, or performing an ablation procedure on at least some ghrelin producing cells present within the stomach and/or intestines are also contemplated. These means may be provided alone or in concert with any other means for regulating activation of ghrelin producing cells within a stomach and/or intestines disclosed herein, in order to achieve the desired effect of treating or curing weight disorders, promoting learning and memory functions, treating stress-induced depression, and/or promoting healthy sleep duration.

BRIEF DESCRIPTION OF THE DRAWINGS

The invention will be more fully understood from the following detailed description taken in conjunction with the accompanying drawings, in which:

FIG. 6A is a cross-sectional view of a passive biological one-way valve in an open position.

FIG. 6B is a cross-sectional view of a passive biological one-way valve in a closed position.

FIG. 10C is a schematic view of a human stomach at a third step of a modified Magenstrasse and Mill (M&M) type surgical procedure.

FIG. 10D is a schematic view of a human stomach at a fourth step of a modified Magenstrasse and Mill (M&M) type surgical procedure.

FIG. 15A is a schematic partially transparent view of a human stomach following a first step in a transoral introduction and laparoscopic fixation of a barrier.

FIG. 15B is a schematic partially transparent view of a human stomach following a second step in a transoral introduction and laparoscopic fixation of a barrier.

FIG. 15C is a schematic view of a human stomach following a third step in a transoral introduction and laparoscopic fixation of a barrier.

FIG. 15D is a schematic view of a human stomach following a transoral introduction and laparoscopic fixation of a barrier and details thereof.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
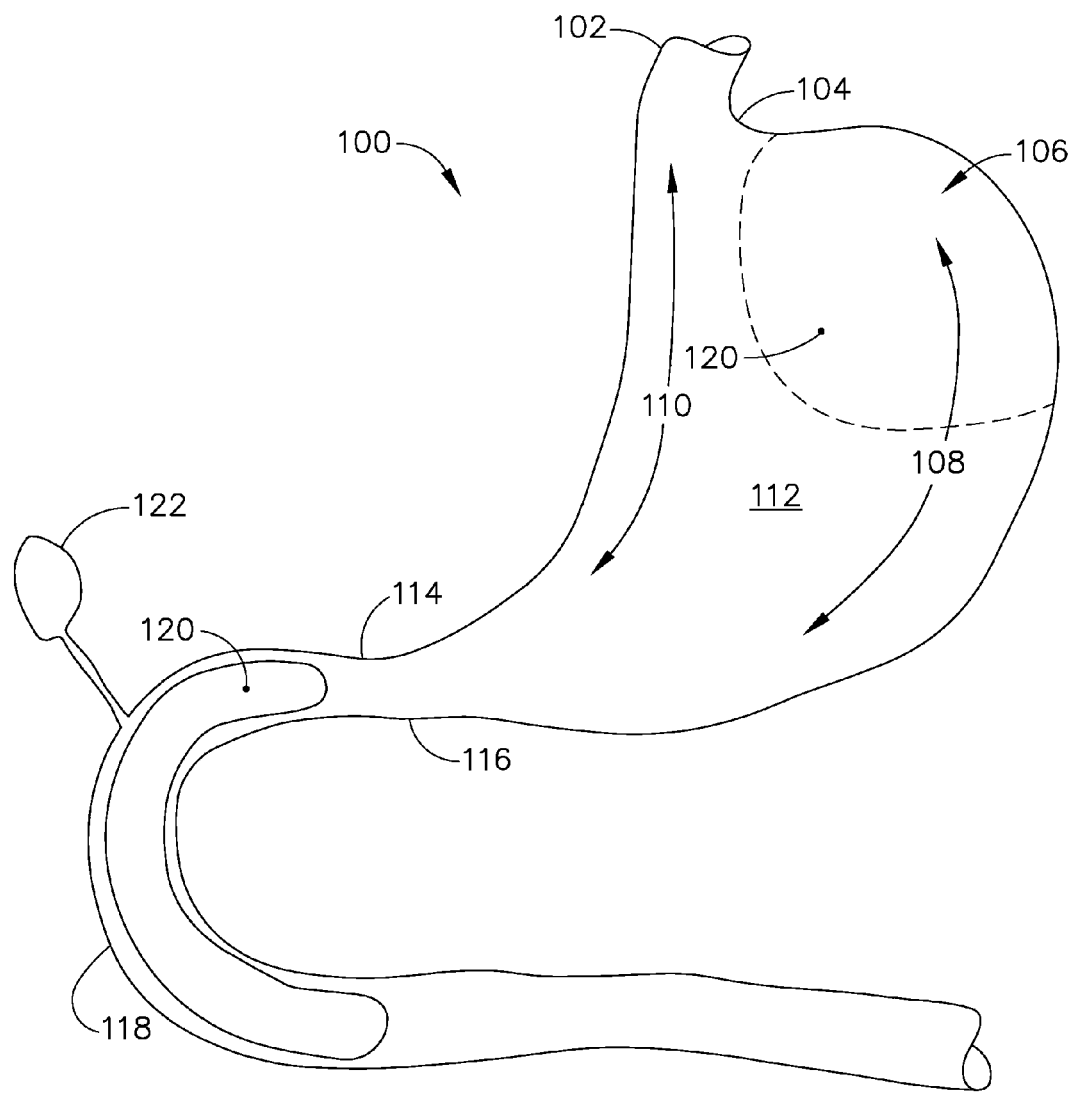
FIG. 1 is a schematic view of a human stomach.

FIG. 1 is a schematic view of a human stomach 100. Esophagus 102, which meets stomach 100 at antrum 104, serves as an inlet for ingested food content. At the uppermost region of stomach 100 resides fundus 106. Fundus 106 is the region of the stomach where most of the ghrelin hormone producing cells reside. Stomach 100 is generally defined by greater curvature 108 and lesser curvature 110, and is bound by anterior wall 112. At the lowermost region of the stomach reside angular notch 114, pylorus 116 and duodenum 118. Together, angular notch 114, pylorus 116 and duodenum 118 serve as an outlet for the contents of the stomach to pass into the intestines (not shown); the digestive process being aided by gall bladder 122. Ghrelin expression zones 120 are defined within stomach 100 in areas generally defined by fundus 106 and duodenum 118.

Figure 2:
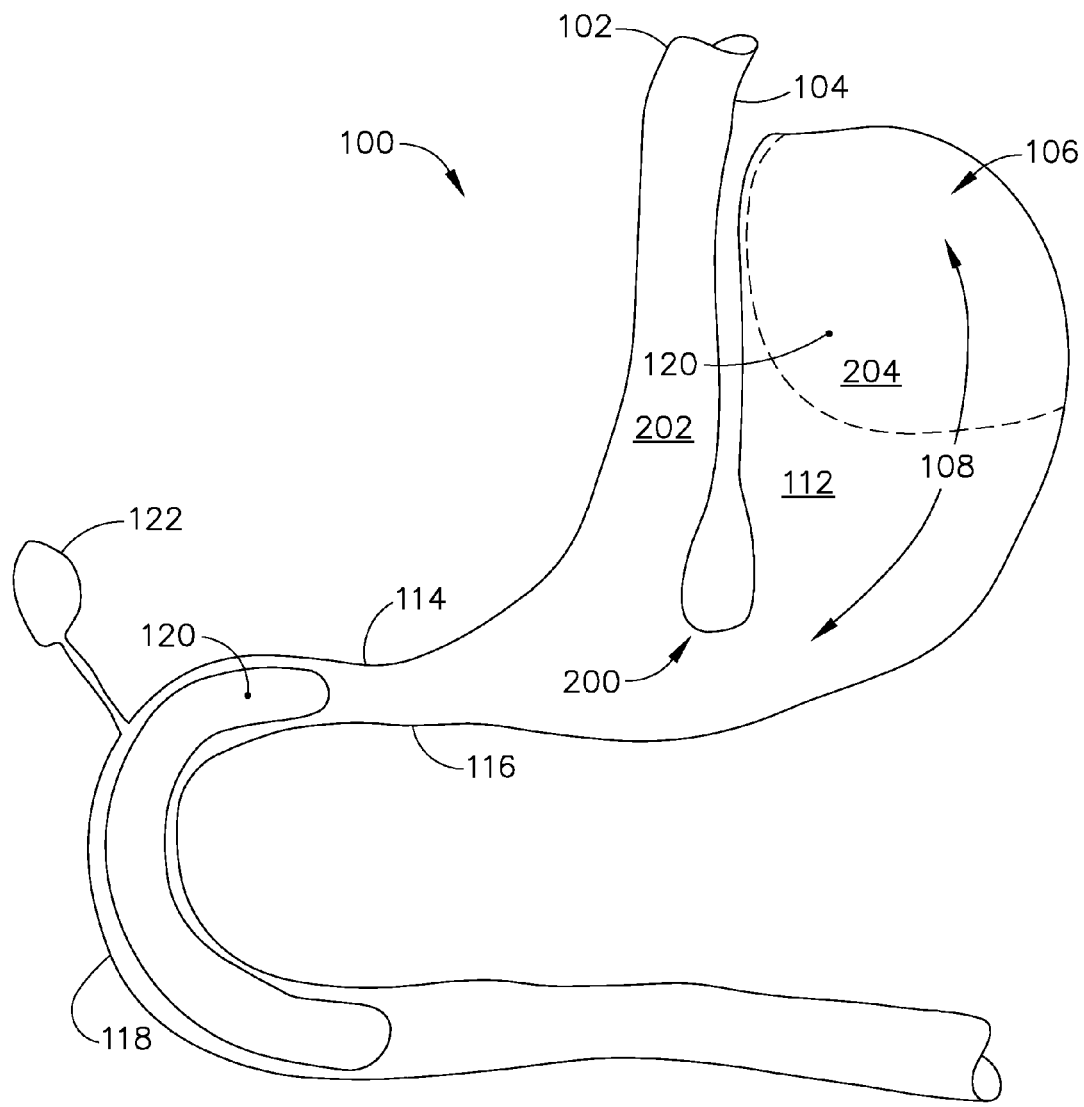
FIG. 2 is a schematic view of a human stomach following a Magenstrasse and Mill (M&M) surgical procedure.

FIG. 2 is a schematic view of human stomach 100 following a Magenstrasse and Mill (M&M) surgical procedure. The M&M surgical procedure is generally accomplished by creating a vertical transection, division or separation 200 of the gastric cavity of stomach 100 generally along lesser curvature 110 from antrum 104 to a point roughly 4-6 cm from pylorus 116. A transorally delivered bougie (not shown) is often placed into the pylorus. The bougie is pressed against lesser curvature 110 with a stapling device (not shown) and helps determine the location of separation 200. The size of the bougie chosen by the surgeon aids in determining the size of the lumen of first stomach chamber 202. The bougie also helps the surgeon create a lumen in chamber 202 that is uniform in diameter. As may be appreciated, the performance of an M&M surgical procedure serves the function of partitioning stomach into a first chamber 202 and a second chamber 204. First chamber 202 contains and permits flow therethrough of food content and dietary lipids (not shown). Second chamber 204 contains the bulk of the ghrelin hormone producing cells present in stomach 100. It should be appreciated that similar procedures for separating the stomach, whether physically or virtually are contemplated and may be performed in place of or in concert with the M&M surgical procedure disclosed herein. Details of such a procedure are disclosed herein with respect to FIGS. 10A-10E.

Figure 3:
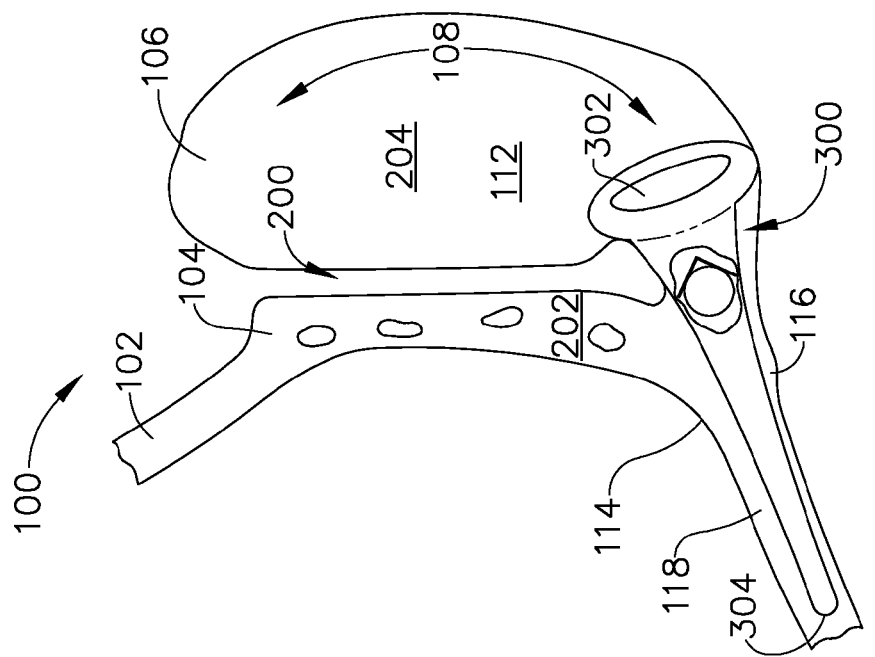
FIG. 3 is schematic partially transparent view of a human stomach following a Magenstrasse and Mill (M&M) surgical procedure and implantation of a controlled evacuation device.

FIG. 3 is schematic partially transparent view of human stomach 100 following a Magenstrasse and Mill (M&M) surgical procedure and implantation of a controlled evacuation device 300. In this particular embodiment, controlled evacuation device 300 is an implanted device having a tubular configuration with an internal bore passing therethrough, thereby defining an inlet 302 and an outlet 304. In this particular embodiment, controlled evacuation device 300 is illustrated as a conical or funnel shaped device where inlet 302 substantially surrounds the space between vertical separation 200 and the bottom portion of anterior wall 112 to substantially create a seal between first chamber 202 and second chamber 204, although it should be understood that various other shapes may be employed by one having ordinary skill in the art without departing from the scope of the present invention. Accordingly, in this embodiment, controlled evacuation device 300 may prevent contact within the stomach of the non-activated ghrelin cells and dietary lipids of first chamber 202 in order to induce or maintain a fat burning metabolic state, thereby causing weight loss in an obese patient. As will be discussed in greater detail later herein, controlled evacuation device 300 may comprise a valve which is functional to provide controlled one-way fluid flow therethrough, and to prevent retrograde flow of food content and dietary lipids through controlled evacuation device 300 by way of peristaltic stomach motions. As may be appreciated, controlled evacuation device 300 may have alternate forms and placements within stomach 100 without departing from the scope of the present invention.

Figure 4:
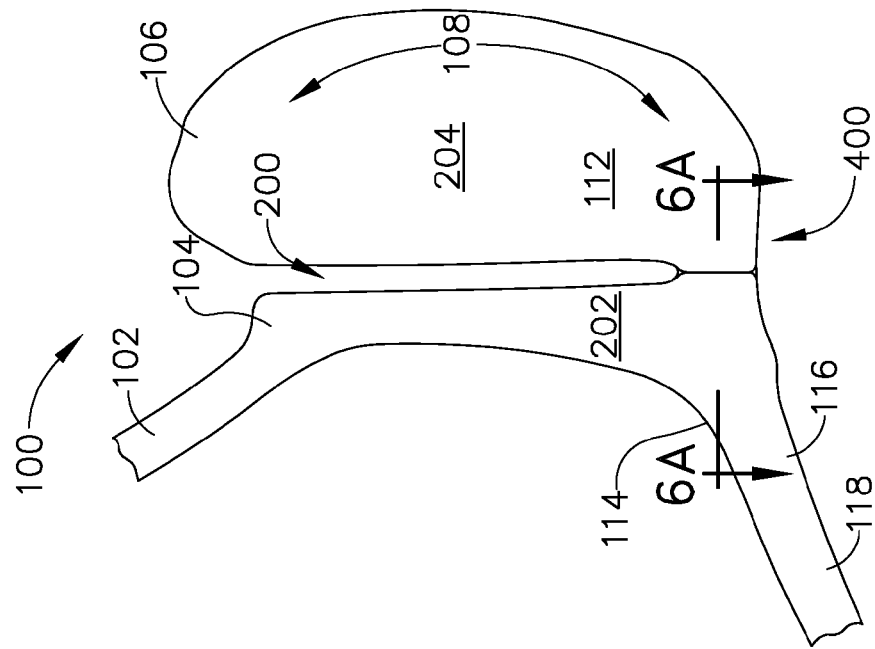
FIG. 4 is a schematic view of a human stomach following a Magenstrasse and Mill (M&M) surgical procedure and creation of a passive biological one-way valve.

FIG. 4 is a schematic view of human stomach 100 following a Magenstrasse and Mill (M&M) surgical procedure and creation of a passive biological one-way valve 400. In this particular embodiment, passive biological one-way valve 400 is functional to regulate the contact between dietary lipids of first chamber 202 and the non-activated ghrelin cells contained within second chamber 204 in order to achieve a desired effect. Passive biological one-way valve 400 may be formed, for example, via tissue folding or tissue removal. Cross-sectional views of a passive biological one-way valve taken along section line 6A-6A will be discussed in greater detail later herein with respect to FIGS. 6A and 6B.. Further, passive biological one-way valve 400 may also include an implantable prosthetic device such as a one-way osmotic membrane. As may be appreciated, passive biological one-way valve 400 may have alternate forms and placements within stomach 100 without departing from the scope of the present invention.

Figure 5A:
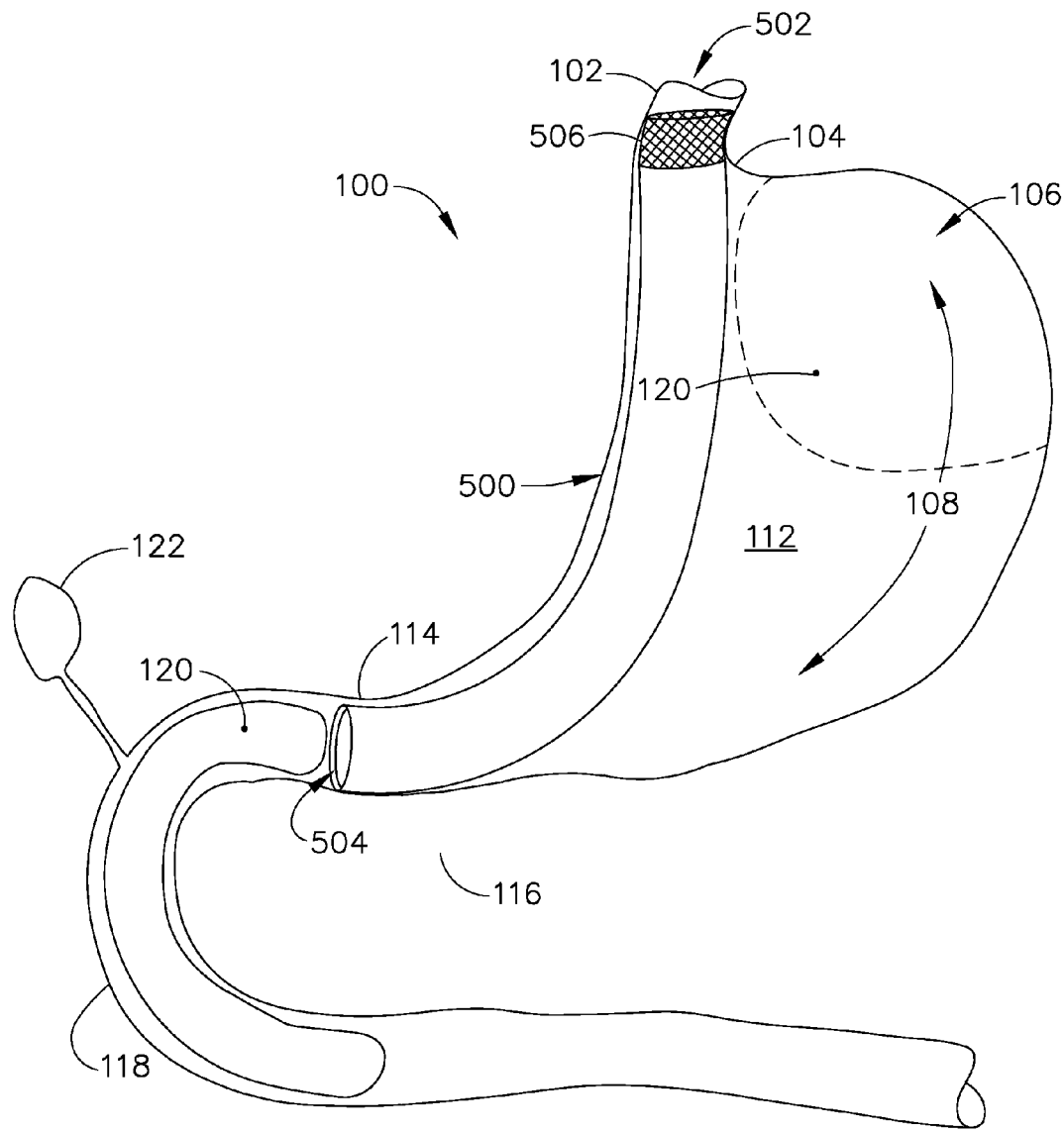
FIG. 5A is a schematic partially transparent view of a human stomach following the implantation of a gastric sleeve.
Figure 5B:
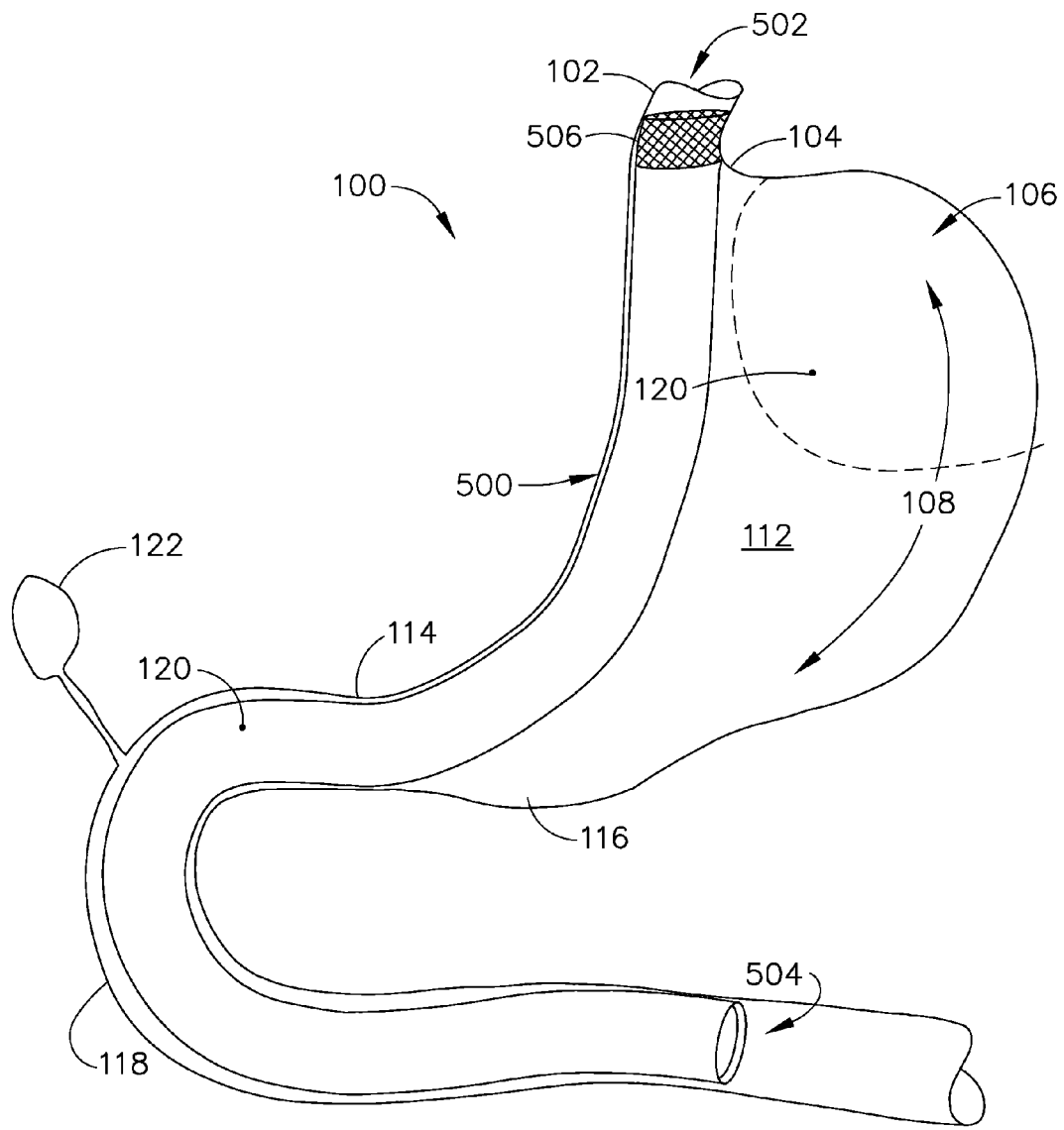
FIG. 5B is a schematic partially transparent view of a human stomach following the implantation of a gastric sleeve.

FIGS. 5A and 5B are schematic partially transparent views of human stomach 100 following the implantation of a gastric sleeve 500. In these particular embodiments, gastric sleeve 500 is an implanted device having a tubular configuration with an internal bore passing therethrough, thereby defining an inlet 502 and an outlet 504. In these particular embodiments, gastric sleeve 500 is secured at its inlet 502 to esophagus 102 near antrum 104 via anchoring stent 506. In FIG. 5A, outlet 504 extends to a point beyond pylorus 116, but terminates prior to ghrelin expression zone 120 of duodenum 118. In FIG. 5B, outlet 504 extends to a point beyond ghrelin expression zone 120 of duodenum 118. In this manner, the length of gastric sleeve 500 may be tailored to the specific needs of the patient, as determined by their physician without departing from the scope of the present invention. Accordingly, food content and dietary lipids are effectively separated from the ghrelin hormone producing cells present in fundus 106 and/or duodenum 118, thereby preventing activation of ghrelin by the enzyme Ghrelin-Octanoyl Acyl-Transferase (GOAT). This isolation may aid in reducing or eliminating hunger sensations, as well as inducing or maintaining a fat burning metabolic state, thereby causing weight loss in an obese patient. As may be appreciated, gastric sleeve 500 may have alternate forms and placements within stomach 100 with the primary function remaining as separating food content and dietary lipids from the ghrelin hormone producing cells present in fundus 106. Further, it should be understood that known gastric sleeves and sleeve gastrectomy methods may be employed, without changing or altering the scope of the present invention.

FIG. 6A is a cross-sectional view of a passive biological one-way valve 400 in an open position, as taken along section line 6A-6A of FIG. 4. As disclosed previously herein, passive biological one-way valve 400 may be formed, for example, via tissue plication or tissue removal. Accordingly, in this particular embodiment, passive biological one-way valve 400 includes a first tissue fold 602 and a second tissue fold 604 which cooperate to form a valve which separates second chamber 204 of stomach 100 from the formed outlet chamber 606. In the open position of FIG. 6A, the stomach fluids contained within second chamber 204 are free to be evacuated into outlet chamber 606, and subsequently through outlet passage 608. As may be appreciated, passive biological one-way valve 400 may have alternate forms (e.g., one or more plications may be created to obtain the desired effect) and placements within stomach 100 with the primary function remaining as controlling evacuation of stomach fluids from second chamber 204.

FIG. 6B is a cross-sectional view of a passive biological one-way valve 400 in a closed position, as taken along section line A-A of FIG. 4. As disclosed previously herein, passive biological one-way valve 400 may be formed, for example, via tissue plication or tissue removal. Accordingly, in this particular embodiment, passive biological one-way valve 400 includes a first tissue fold 602 and a second tissue fold 604 which cooperate to form a valve which separates second chamber 204 of stomach 100 from the formed outlet chamber 606. In the closed position of FIG. 6B, the stomach fluids contained within second chamber 204 are collected before being evacuated into outlet chamber 606, and subsequently through outlet passage 608. In this embodiment, dietary lipids are prevented from contacting the ghrelin producing cells in second chamber 204. As may be appreciated, passive biological one-way valve 400 may have alternate forms and placements within stomach 100 with the primary function remaining as controlling evacuation of stomach fluids from second chamber 204.

Figure 7:
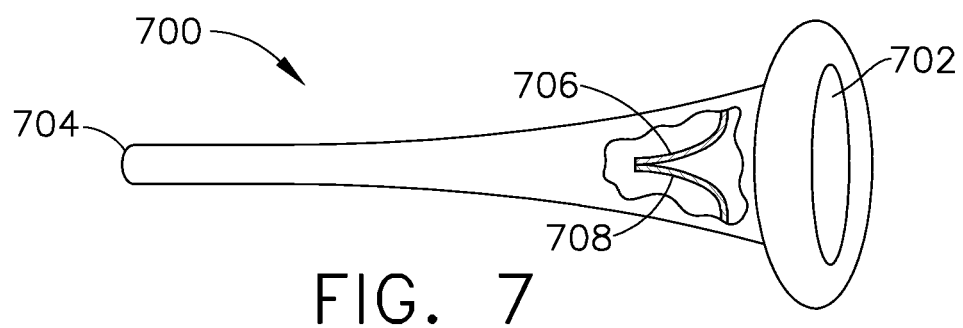
FIG. 7 is a schematic partially transparent view of a controlled evacuation device comprising a duck bill valve.

FIG. 7 is a schematic partially transparent view of a controlled evacuation device 700 comprising a duck bill valve. In this particular embodiment, controlled evacuation device 700 is an implanted device having a tubular configuration with an internal bore passing therethrough, thereby defining an inlet 702 and an outlet 704. Within the internal bore resides a duck bill valve formed by a first elongated member 706 and a second elongated member 708. First elongated member 706 and a second elongated member 708 are resiliently biased to a normally closed configuration as seen in FIG. 7, but allow for passage of materials therethrough. In one embodiment, the material passing therethrough is the stomach fluids contained within second chamber 204 as described previously herein with respect to FIG. 3.

Figure 8:
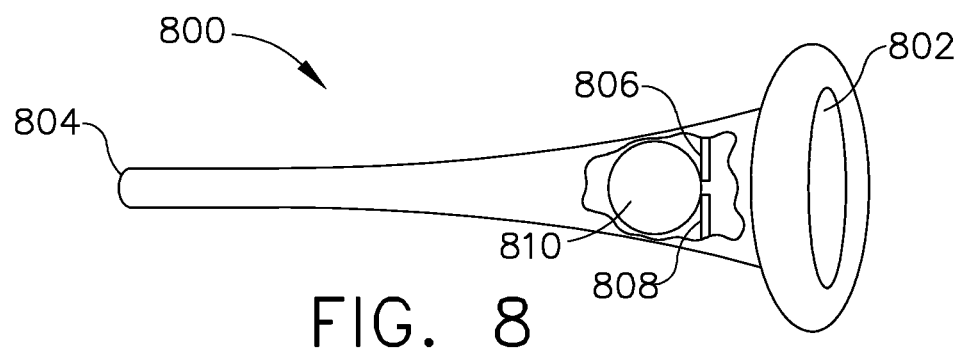
FIG. 8 is a schematic partially transparent view of a controlled evacuation device comprising an internal ball valve.

FIG. 8 is a schematic partially transparent view of a controlled evacuation device 800 comprising an internal ball valve. In this particular embodiment, controlled evacuation device 800 is an implanted device having a tubular configuration with an internal bore passing therethrough, thereby defining an inlet 802 and an outlet 804. Within the internal bore resides a ball valve formed by a first elongated member 806 and a second elongated member 808 which interact with a ball 810. Ball 810 may be resiliently biased to a normally closed configuration as seen in FIG. 8, but allow for passage of materials therethrough. In one embodiment, the material passing therethrough is the stomach fluids contained within second chamber 204 as described previously herein with respect to FIG. 3. As may be appreciated, ball 810 may be constructed of a suitable material such as Polyetheretherketone (PEEK) or silicone and have a suitable size and shape for use within a human stomach.

Figure 9:
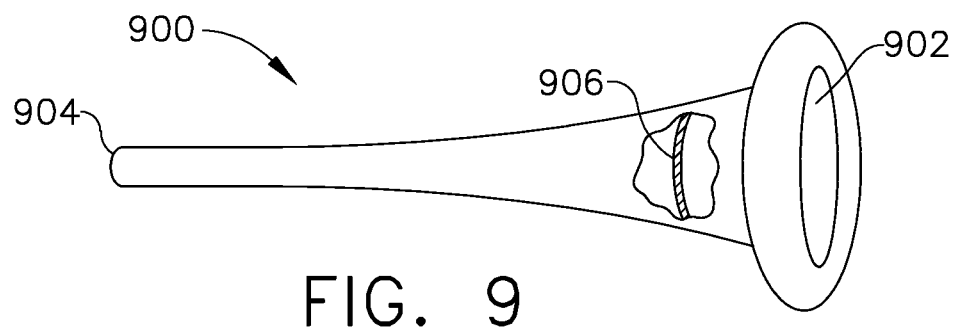
FIG. 9 is a schematic partially transparent view of a controlled evacuation device comprising an osmotic membrane.

FIG. 9 is a schematic partially transparent view of a controlled evacuation device 900 comprising an osmotic membrane. In this particular embodiment, controlled evacuation device 900 is an implanted device having a tubular configuration with an internal bore passing therethrough, thereby defining an inlet 902 and an outlet 904. Within the internal bore resides an osmotic membrane 906. Osmotic membrane 906 allows for one-way fluid passage therethrough. In one embodiment, the fluid passing therethrough is the stomach fluids contained within second chamber 204 as described previously herein with respect to FIG. 3.

Figure 10A:
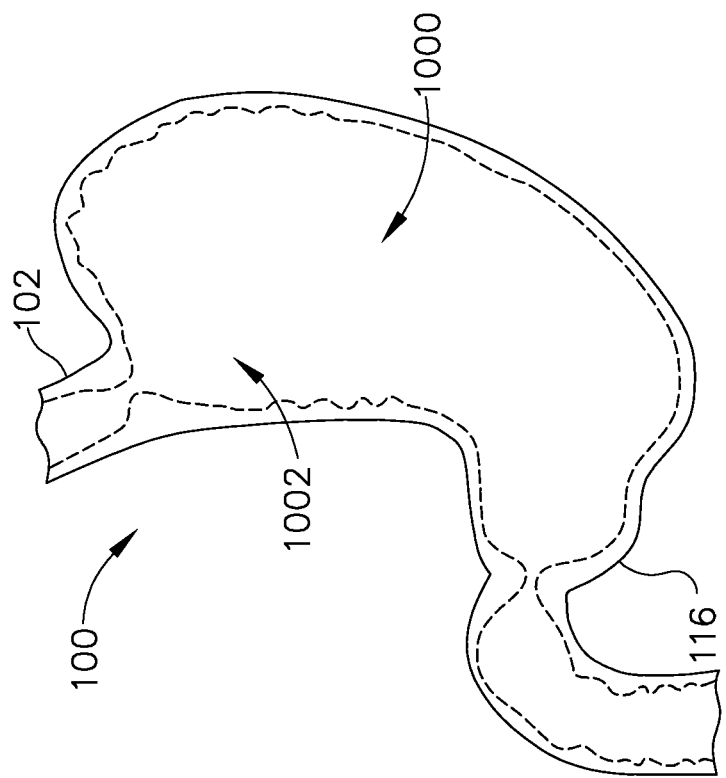
FIG. 10A is a schematic view of a human stomach at a first step of a modified Magenstrasse and Mill (M&M) type surgical procedure.
Figure 10B:
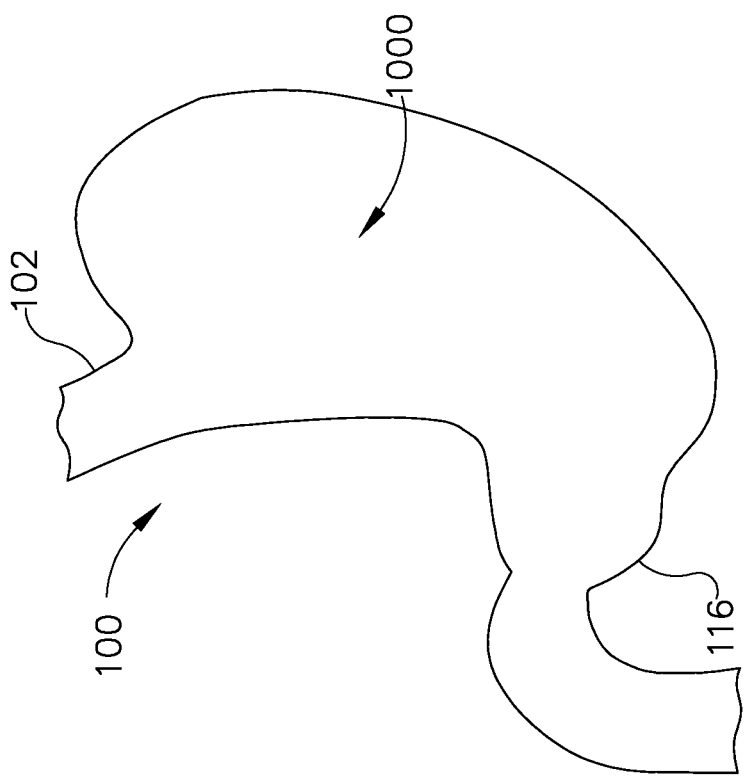
FIG. 10B is a schematic view of a human stomach at a second step of a modified Magenstrasse and Mill (M&M) type surgical procedure.
Figure 10E:
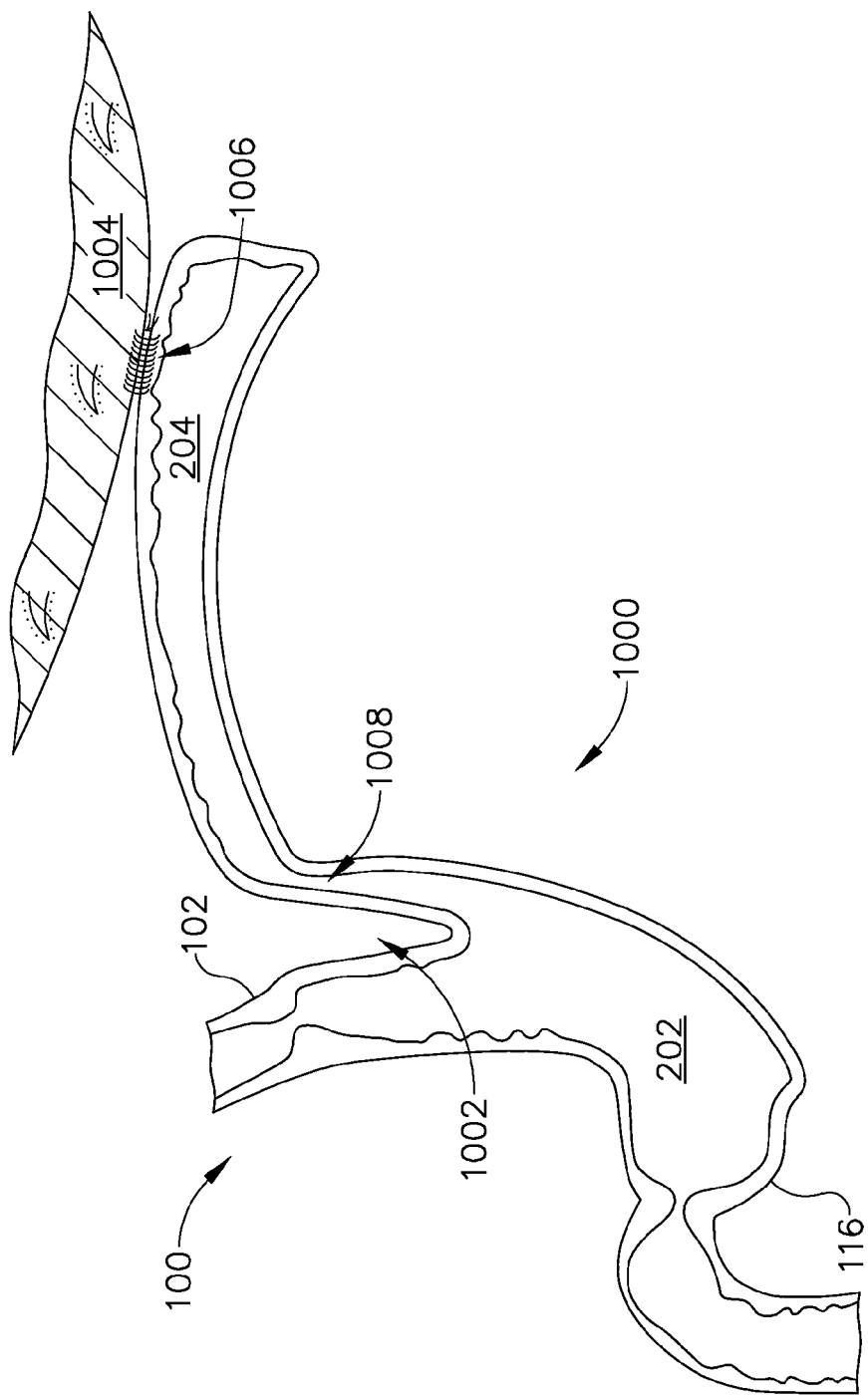
FIG. 10E is a schematic view of a human stomach at a fifth step of a modified Magenstrasse and Mill (M&M) type surgical procedure.

FIGS. 10A-10E illustrate a schematic view of human stomach 100 undergoing the basic steps of a modified Magenstrasse and Mill (M&M) type surgical procedure. In FIG. 10A, a first division or separation 1000 is created in stomach 100. In FIG. 10B, a second division or separation 1002 is created in stomach 100. In FIG. 10C, first division or separation 1000 is separated to create two distinct stomach chambers; first stomach chamber 202 and second stomach chamber 204. In FIG. 10D, second division or separation 1002 is also separated to further define first stomach chamber 202 and second stomach chamber 204. In FIG. 10E, second stomach chamber 204 is secured to inert structural tissue 1004 in the abdominal cavity of the patient by sutures 1006 or the like. In this manner, narrow passage 1008 between first division or separation 1000 and second division or separation 1002 serves as the only fluid communication passage between first stomach chamber 202 and second stomach chamber 204, thereby controlling the fluid communication between the dietary lipids contained within first stomach chamber 202 and the ghrelin hormone producing cells present second stomach chamber 204. This in turn prevents activation of the non-activated ghrelin cells which will induce or maintain a fat burning metabolic state, thereby causing weight loss in an obese patient. As may be appreciated, passage 1008 may further include a valve means (not shown) which may, for example, comprise either an implanted mechanical device or a surgically created biological one-way valve which have been detailed previously herein in other embodiments.

Figure 11:
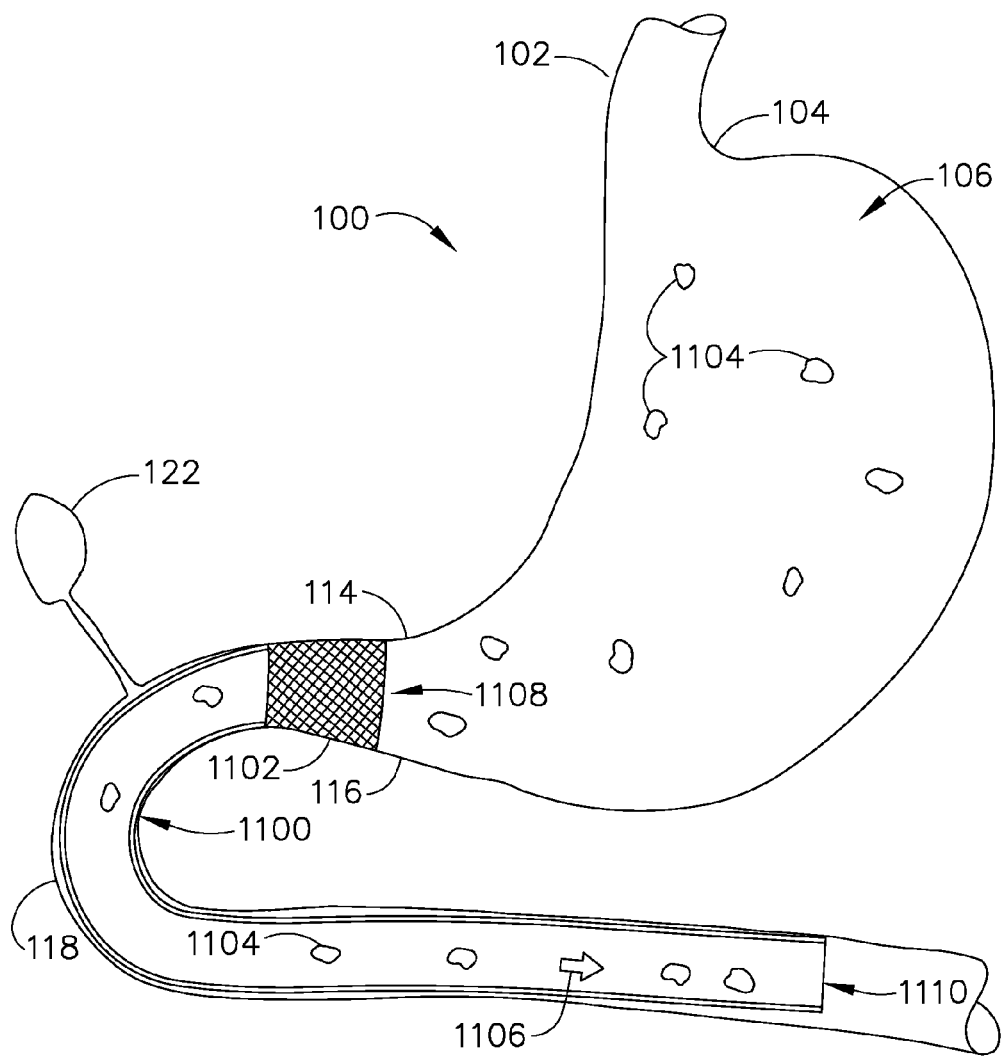
FIG. 11 is a schematic partially transparent view of a human stomach following the implantation of a duodenal sleeve.

FIG. 11 is a schematic partially transparent view of human stomach 100 following the implantation of a duodenal sleeve 1100. In this particular embodiment, duodenal sleeve 1100 is anchored at its inlet 1108 by anchoring stent 1102 within duodenum 118. In these particular embodiments, duodenal sleeve 1100 is an implanted device having a tubular configuration with an internal bore passing therethrough, thereby defining an inlet 1108 and an outlet 1110. In FIG. 11, outlet 1110 of duodenal sleeve 1100 extends to a point beyond ghrelin expression zone 120 of duodenum 118 (see FIG. 1). In this manner, the length of duodenal sleeve 1100 may be tailored to the specific needs of the patient, as determined by their physician without departing from the scope of the present invention. Accordingly, food content and dietary lipids 1104 pass through duodenal sleeve 1100 in a direction indicated by flow arrow 1106 and are effectively separated from the ghrelin hormone producing cells present in duodenum 118, thereby preventing activation of ghrelin by the enzyme Ghrelin-Octanoyl Acyl-Transferase (GOAT). This isolation may aid in reducing or eliminating hunger sensations, as well as inducing or maintaining a fat burning metabolic state, thereby causing weight loss in an obese patient. As may be appreciated, duodenal sleeve 1100 may have alternate forms and placements within duodenum 118 with the primary function remaining as separating food content and dietary lipids from the ghrelin hormone producing cells present in duodenum 118. Further, it should be understood that known duodenal sleeves and sleeve gastrectomy methods may be employed, without changing or altering the scope of the present invention.

Figure 12:
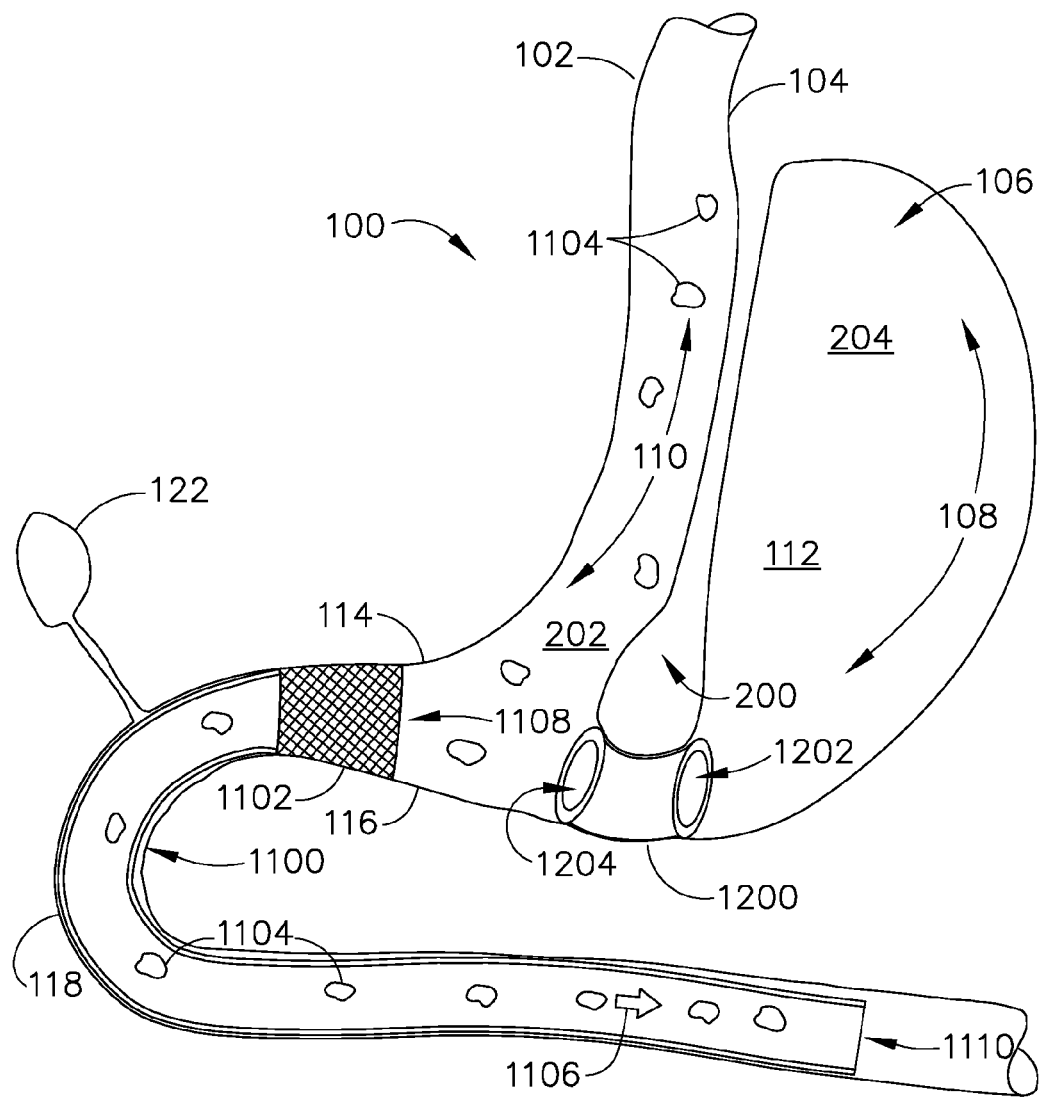
FIG. 12 is schematic partially transparent view of a human stomach following a Magenstrasse and Mill (M&M) surgical procedure and implantation of a controlled evacuation device and a duodenal sleeve.

FIG. 12 is schematic partially transparent view of human stomach 100 following a Magenstrasse and Mill (M&M) surgical procedure and implantation of a controlled evacuation device 1200 and a duodenal sleeve 1100. Controlled evacuation device 1200 includes an inlet 1202 and an outlet 1204 and comprises a valve which is functional to provide controlled one-way fluid flow therethrough, and to prevent retrograde flow of food content and dietary lipids through controlled evacuation device 1200 by way of peristaltic stomach motions. Accordingly, in this embodiment, controlled evacuation device 1200 may prevent contact within the stomach of the non-activated ghrelin cells and dietary lipids of first chamber 202 in order to induce or maintain a fat burning metabolic state, thereby causing weight loss in an obese patient. As may be appreciated, controlled evacuation device 1200 may have alternate forms (e.g., a passive biological one-way valve as in FIG. 4 above) and placements within stomach 100 without departing from the scope of the present invention. The M&M procedure of FIG. 12 is equivalent to that of the M&M procedure detailed previously herein with respect to FIG. 2. The implantation of duodenal sleeve 1100 is equivalent to that of the procedure detailed previously herein with respect to FIG. 11.

Figure 13:
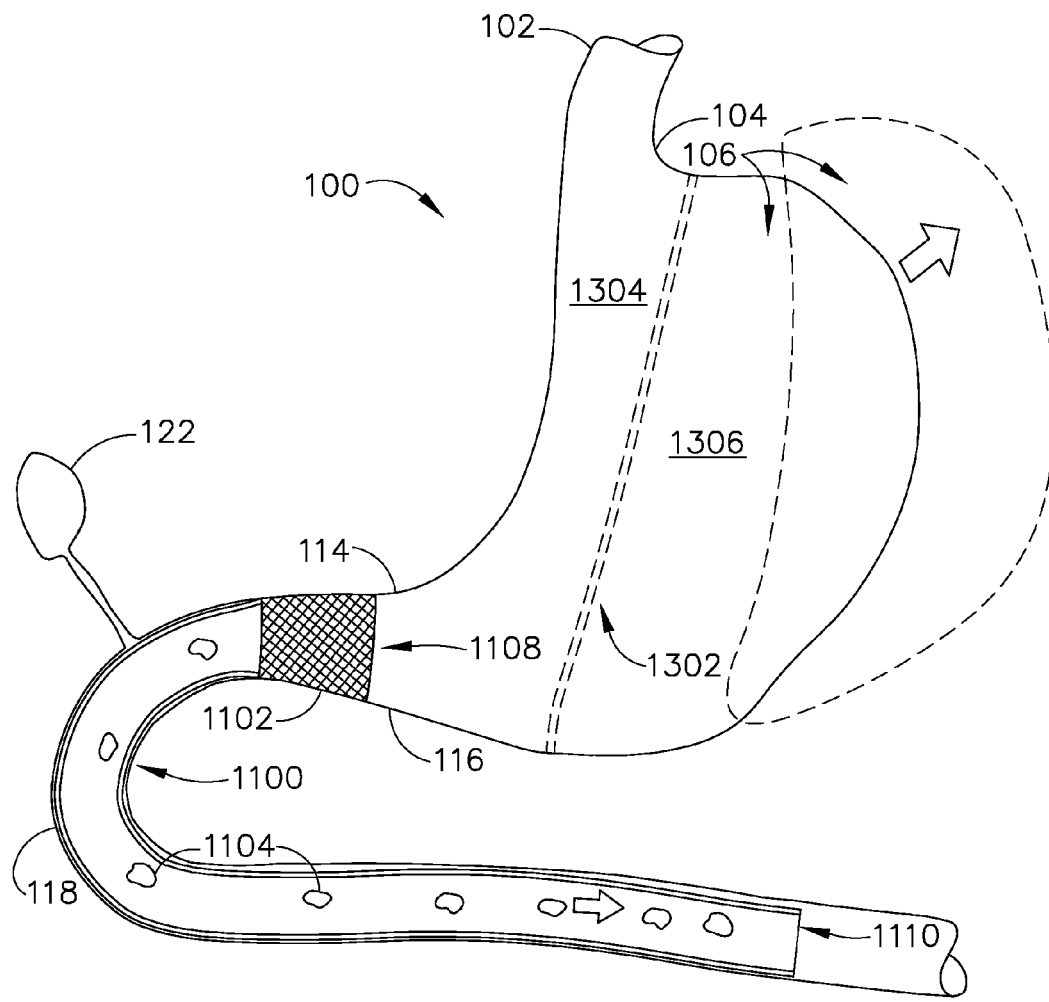
FIG. 13 is schematic partially transparent view of a human stomach following a sleeve gastrectomy procedure and implantation of a duodenal sleeve.

FIG. 13 is schematic partially transparent view of human stomach 100 following a sleeve gastrectomy procedure and implantation of a duodenal sleeve 1100. In FIG. 13, a division or separation 1302 is created in stomach 100 in order to create two distinct stomach portions; first portion 1304 and second portion 1306. In this embodiment, second portion 1306 comprising fundus 106 is excised leaving stomach 100 having portion 1304 as its new effective volume. In this manner, the ghrelin producing portions of fundus 106 are removed from the body and are therefore incapable of being contacted by the dietary lipids and food content within stomach 100. The implantation of duodenal sleeve 1100 is equivalent to that of the procedure detailed previously herein with respect to FIG. 11.

Figure 14A:
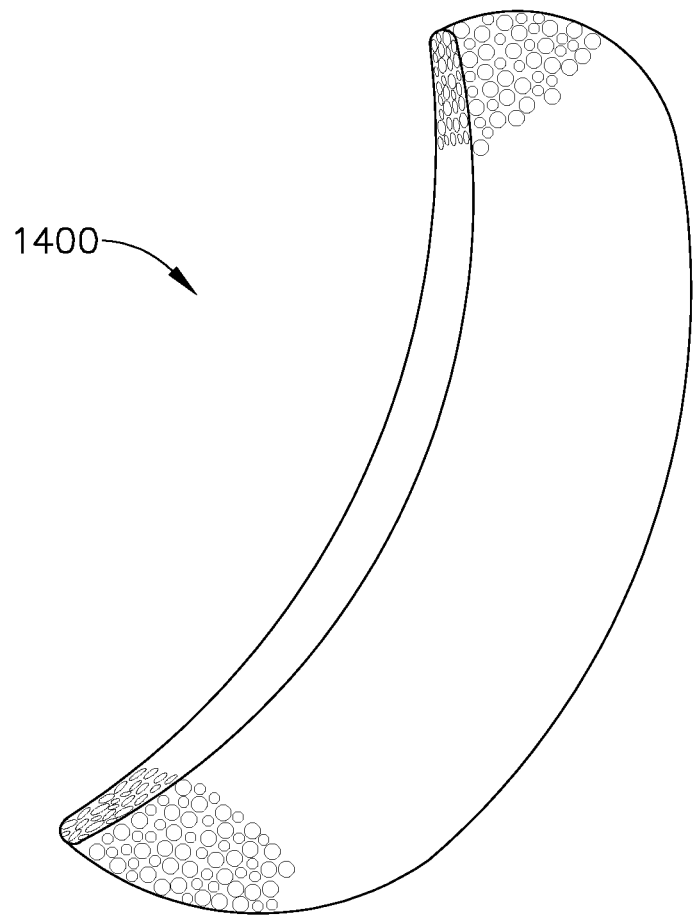
FIG. 14A is schematic view of a unitary implantable hydrophilic foam barrier.
Figure 14C:
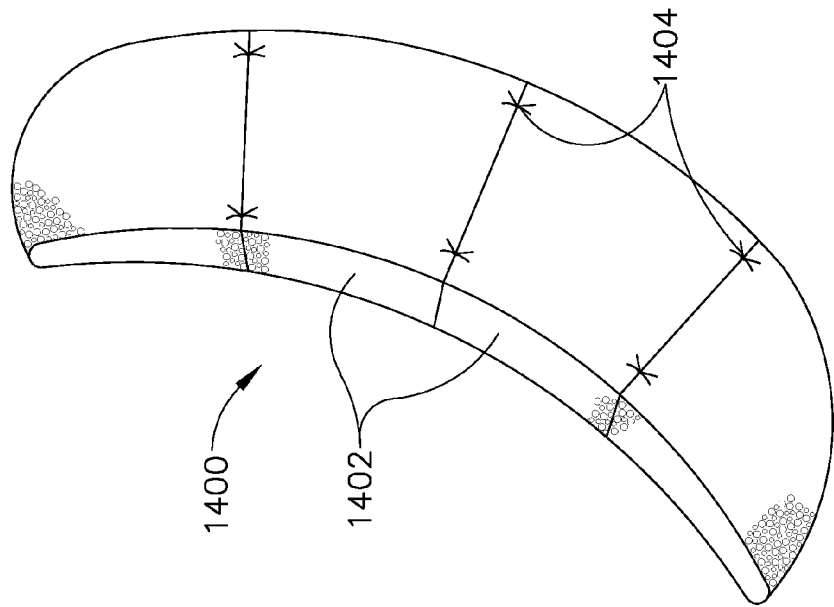
FIG. 14C is schematic view of a segmented ingestible hydrophilic foam barrier after suturing.
Figure 14B:
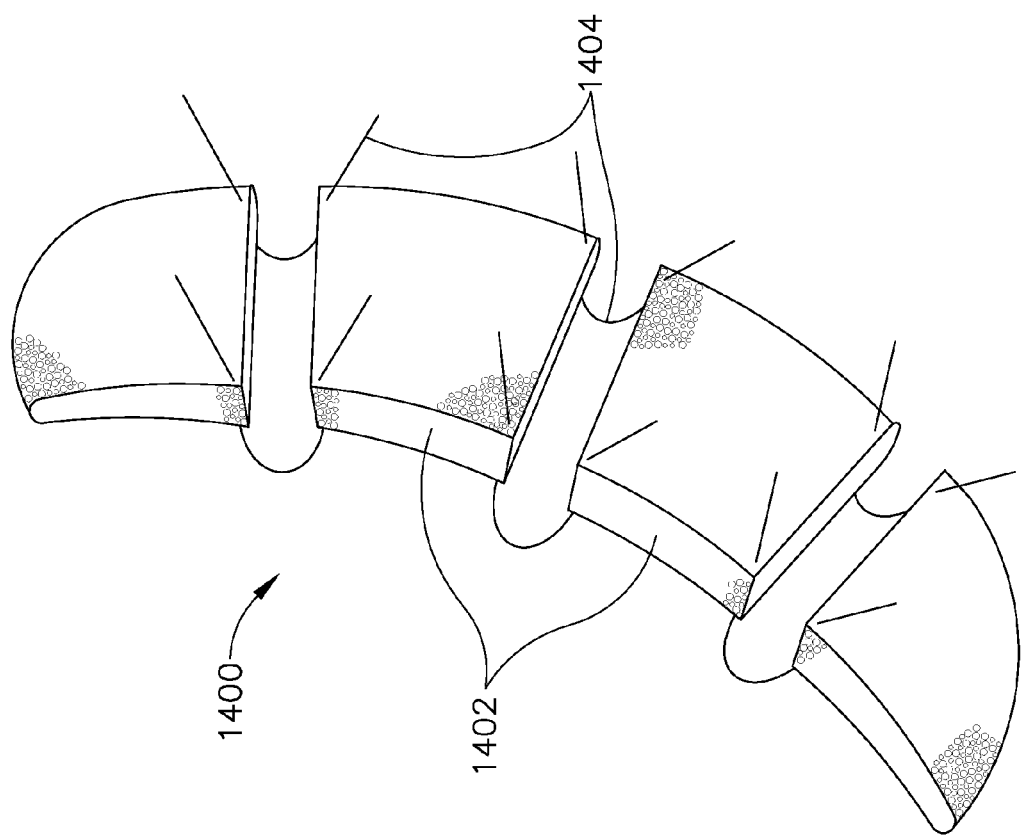
FIG. 14B is schematic view of a segmented ingestible hydrophilic foam barrier prior to suturing.

FIGS. 14A-C are schematic views of hydrophilic foam barrier 1400. In FIG. 14A, hydrophilic foam barrier 1400 is a unitary implantable device, whereas in FIGS. 14B and 14C barrier 1400 is a segmented ingestible device. In these figures, barrier 1400 is constructed from multiple smaller sections 1402. Each section 1402 would be small enough to pass in the expanded state shown. One embodiment of a construction method would be to hold the sections together with bioabsorbable suture 1404. That way, barrier 1400 could be implanted in one easily maneuverable piece, but would break up into passable sections in the unlikely event that it becomes dislodged from the gastric fixturing means (discussed below). The idea described in this document uses a moist barrier to repel lipids from areas of the stomach or small bowel that contain GOAT. In one embodiment, barrier 1400 is a highly hydrophilic and is constructed of a porous material.

FIGS. 15A-C are schematic partially transparent views of human stomach 100 following a transoral introduction and laparoscopic fixation of hydrophilic foam barrier 1400. FIG. 15A illustrates a first step in the process wherein barrier 1400 is rolled, compressed and inserted into stomach 100 orally. FIG. 15B illustrates a second step in the process wherein barrier 1400 is unrolled and positioned in fundus 106 using a flexible endoscope with standard tools (not shown). FIG. 15C illustrates a third step in the process wherein using a laparoscopic device 1500, the anterior and posterior layers of stomach 100 are forced into contact with barrier 1400, not compressing the barrier fully. Fasteners 1502 are inserted through the anterior stomach layer, barrier 1400 and the posterior stomach layer in order to hold barrier 1400 in place.

Figure 15E:
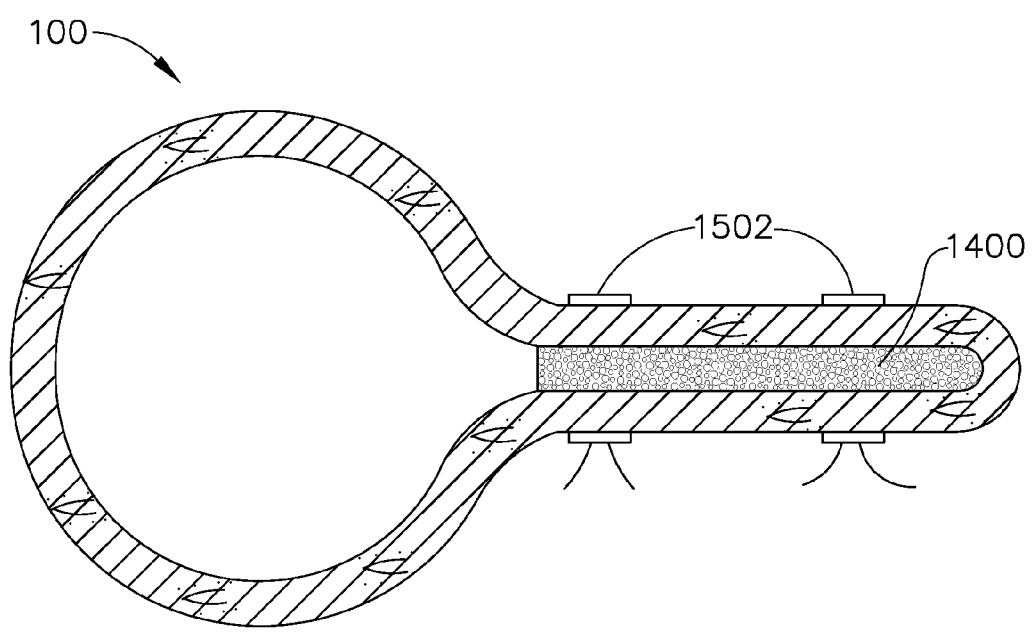
FIG. 15E is a cross sectional view of a human stomach following a transoral introduction and laparoscopic fixation of a barrier and details thereof.

FIGS. 15D-E are a schematic view and cross sectional view respectively of human stomach 100 following a transoral introduction and laparoscopic fixation of an hydrophilic foam barrier 1400 and details thereof. As shown and described previously herein with respect to FIGS. 15A-C, FIG. 15D illustrates barrier 1400 fastened between the anterior stomach layer and the posterior stomach layer via fasteners 1502 and further includes a section line A-A. FIG. 15E as taken along section line A-A illustrates barrier 1400 fastened between the anterior stomach layer and the posterior stomach layer via fasteners 1502 in order to be better understood.

Figures 15F, 15G:
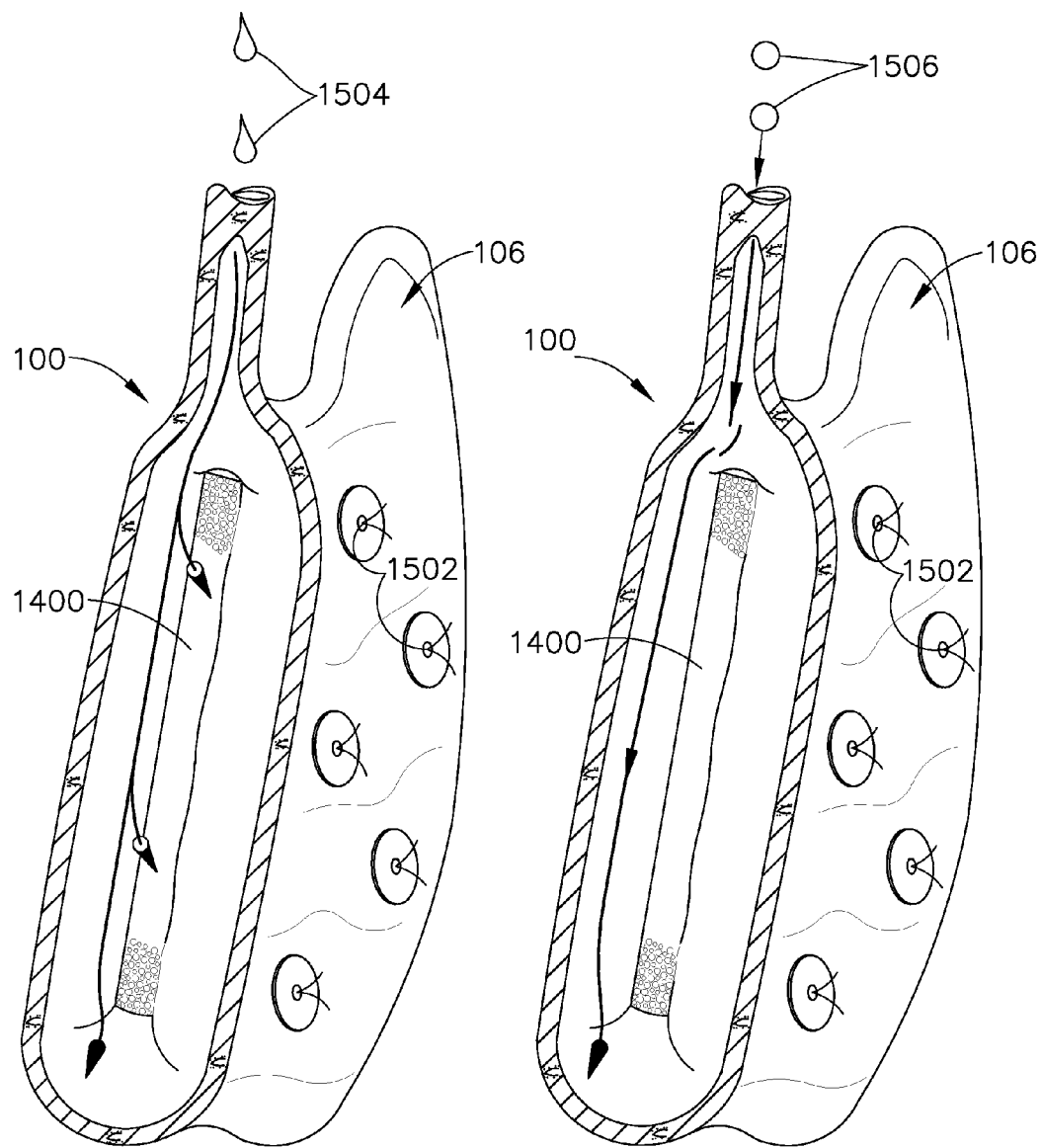
FIG. 15F is a schematic partially transparent view of a human stomach following a transoral introduction and laparoscopic fixation of a barrier illustrating a water path within the stomach.
FIG. 15G is a schematic partially transparent view of a human stomach following a transoral introduction and laparoscopic fixation of a barrier illustrating a lipid path within the stomach.

FIGS. 15F-G is are schematic partially transparent views of human stomach 100 following a transoral introduction and laparoscopic fixation of a barrier illustrating a water path and a lipid path respectively within stomach 100. In FIG. 15F a portion of water 1504 introduced by ingestion is retained in barrier 1400. Also, secretions from fundus area 106 of stomach 100 can pass through barrier 1400 for drainage, because they are water based. However, as seen in FIG. 15G, ingested lipids 1506 are repelled by barrier 1400 due to the fact that the porous material is engorged with water 1504, and lipids 1506 are hydrophobic. Therefore, it is ensured that lipids 1506 do not contact the GOAT containing tissue within fundus 106. This isolation may aid in reducing or eliminating hunger sensations, as well as inducing or maintaining a fat burning metabolic state, thereby causing weight loss in an obese patient.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

We claim:

1. A method for regulating the activation of ghrelin hormones within a stomach, the method comprising:
   a. dividing a stomach of a patient into a first chamber and a second chamber, wherein said second chamber produces more ghrelin hormones than said first chamber, wherein said step of dividing comprises retaining a matter passageway between said first and second chambers;
   b. establishing one way matter flow between said first and second chambers within said passageway so that mass can flow from only said second chamber to said first chamber;
   c. providing a controlled evacuation device comprising an inlet and an outlet, said controlled evacuation device being capable of permitting controlled evacuation of non-activated ghrelin hormones contained within said second chamber; and
   d. positioning said controlled evacuation device such that said controlled evacuation device is disposed within said matter passageway between said first chamber and said second chamber, and wherein said inlet of said controlled evacuation device is disposed within said second chamber.

2. The method of claim 1 wherein said first chamber is capable of containing and permitting flow therethrough of food content and dietary lipids.

3. The method of claim 1 wherein said second chamber contains the majority of ghrelin hormone producing cells present in the stomach.

4. The method of claim 1 wherein said dividing step is accomplished by a surgical procedure selected from a Magenstrasse and Mill procedure, implantation of a device, and a combination thereof.

5. The method of claim 1 wherein said controlled evacuation device creates a seal between said first chamber and said second chamber.

6. The method of claim 1 wherein said controlled evacuation device defines a conical or funnel shape.

7. The method of claim 1 wherein said controlled evacuation device comprises an elongate tubular device.

8. The method of claim 1 wherein said controlled evacuation device comprises a valve assembly.

9. The method of claim 8 wherein said valve assembly comprises a valve selected from a duck bill valve, a ball valve, a one-way osmotic membrane, or a combination thereof.

10. The method of claim 1 further comprising the step of implanting a gastric sleeve having a tubular configuration and defining an internal bore passing therethrough thereby defining an inlet and an outlet, said gastric sleeve being secured at its inlet to the esophagus of said patient and said outlet being at a location beyond a pylorus of said patient but prior to a ghrelin expression zone of a duodenum of said patient.

11. The method of claim 1 further comprising the step of implanting a gastric sleeve comprising a tubular configuration and an internal bore passing therethrough thereby defining an inlet and an outlet, said gastric sleeve being secured at said inlet to an esophagus of said patient and said outlet terminating after a ghrelin expression zone of a duodenum of said patient.

12. The method of claim 1 wherein food content and dietary lipids are separated from a ghrelin expression zone of said patient.

13. The method of claim 1, further comprising the step of excising said second chamber, wherein said second chamber comprises the fundus of said stomach.

14. The method of claim 1 wherein said method provides a benefit to said patient selected from treatment of weight disorders, treatment of metabolic disorders, promotion of learning functions, promotion of memory functions, treatment of depression, improvement of sleep duration, and combinations thereof.

15. A method of regulating the activation of ghrelin hormones in a patient, the method comprising the steps of:
  a. creating a first division of the stomach of said patient by separating said stomach from a bottom of said stomach toward a top of said stomach such that a first narrow passage is defined at the top of said stomach, said first division creating a first chamber and a second chamber connected by said first passage, wherein said second chamber comprises the majority of ghrelin producing cells; and
  b. creating a second division of said stomach by separating said first chamber of said stomach from the top of said stomach toward the bottom of said stomach such that said second division defines a second narrow passage between said first chamber and said first narrow passage, and wherein said first and second narrow passages control fluid communication between dietary lipids within said first chamber and ghrelin-producing cells of said second chamber.

16. The method of claim 15 wherein said first and second narrow passages comprise a one-way valve.

17. The method of claim 15 wherein said second chamber is secured to inert structural tissue in the abdominal cavity of said patient using sutures.

18. The method of claim 15 wherein activation of ghrelin cells is prevented to induce or maintain a fat burning metabolic state, for a period of time sufficient to cause weight loss in a patient.

* * * * *